United States Patent
Tomioka et al.

[11] Patent Number: 6,036,343
[45] Date of Patent: Mar. 14, 2000

[54] ILLUMINATION SYSTEM FOR ENDOSCOPES

[75] Inventors: Makoto Tomioka; Sayaka Koga, both of Hachioji, Japan

[73] Assignee: Olympus Optical Co., Ltd., Tokyo, Japan

[21] Appl. No.: 09/174,457

[22] Filed: Oct. 19, 1998

[30] Foreign Application Priority Data

Oct. 20, 1997 [JP] Japan .................................. 9-287220

[51] Int. Cl.$^7$ ...................................................... F21V 7/04
[52] U.S. Cl. ........................... 362/574; 362/268; 385/33; 600/177; 600/178
[58] Field of Search .................................... 362/572, 574, 362/268; 385/33, 88; 600/160, 176–178

[56] References Cited

U.S. PATENT DOCUMENTS

| 4,266,534 | 5/1981 | Ogawa | 600/177 |
| 5,143,435 | 9/1992 | Kikuchi | 362/574 |

FOREIGN PATENT DOCUMENTS 5-341127   12/1993   Japan .
6194582    7/1994    Japan .

*Primary Examiner*—James Phan
*Attorney, Agent, or Firm*—Pillsbury Madison & Sutro LLP

[57] ABSTRACT

An illumination system for endoscopes includes a light source device having an arc discharge lamp and a light source optical system; a light guide cable; and a rigid endoscope provided with a light guide on a scope side and an objective optical system, using lenses as a relay optical system. The light source optical system projects the light-emitting section of the arc discharge lamp on the entrance face of the light guide cable at a magnification of approximately 1×, and the light guide cable satisfies the following conditions:

$$0.25 \times Mg1^{1/2} < D_L/D_S < 0.5 \times Mg1^{1/2}$$

$$0.8 < Mg1 \times (D_C/D_L) < 1.2$$

where $D_S$ is the outside diameter of a scope, $D_C$ is the diameter of the light guide cable, $D_L$ is the diameter of the light guide on the scope side, and $Mg1$ is the projection magnification of an optical element interposed between the light guide cable and the light guide on the scope side.

12 Claims, 13 Drawing Sheets

3-MM DIA. RIGID ENDOSCOPE
(RELAY LENS DIA. 2.3 MM
LIGHT GUIDE DIA. 1.2 MM)

4-MM DIA. RIGID ENDOSCOPE
(RELAY LENS DIA. 3.2 MM
LIGHT GUIDE DIA. 1.5 MM)

ILLUMINATION SYSTEM FOR ENDOSCOPES

BACKGROUND OF THE INVENTION

1. Field of the Invention

This invention relates to an illumination system for endoscopes which are widely used in the field of medicine, and in particular, to a rigid endoscope used in the field of surgery.

2. Description of Related Art

Recently, a minimally invasive surgery using an endoscope and special treatment tools has been popularized in the field of surgery of medicine. A disease for which an abdominal operation has been required in the past has come to be treated by the minimally invasive surgery under the endoscope. Thus, in order to relieve social burdens of patients, for example, by reducing the term of hospitalization, it is expected that a surgical operation under the endoscope will be widely developed in the future.

In the surgical operation under the endoscope, the following requirements are now desired.

(1) Reduction in diameter of an endoscope for further promoting the minimally invasive surgery (2) Establishment of an operating room for the exclusive use of the endoscope in which medical instruments can be integrally controlled, without using cables For item (1), a further minimally invasive surgery can be promoted by diminishing the diameter of the endoscope, and the social burdens of patients can be greatly relieved by further reducing the term of hospitalization.

As for item (2), at least 7–8 kinds of instruments are used nowadays for the surgical operation under the endoscope, which is performed by connecting these instruments by tubes or cables.

In a conventional operating room in which the surgical operation under the endoscope is performed, however, as mentioned above, a number of tubes or cables are provided which are means for connecting individual instruments with treatment tools, and they are crossed and extended across a sanitary region and a non-sanitary region, without distinction.

Although conventional instruments used for manipulation employing the endoscope are available in about 10 kinds, individual instruments are all controlled by themselves and thus a systematic work efficiency is considerably impaired. In particular, in the operating room, a plurality of instruments are arranged in disorder around an operating table, and this situation gives rise to the problem that their control is extremely difficult.

In this way, the operating room for the exclusive use of the endoscope stated in item (2) is urgently required, in which instruments including a light source are arranged at some distance away from the operating table. Light emitted from the light source is transmitted to a centralized connector lying on the side of the operating table by a connecting light guide through a ceiling, and the centralized connector has a role like a secondary light source. The establishment of the operating room for the exclusive use of the endoscope eliminates a complicated crossing of tubes or cables around the operating table and enables an operator to devote himself to the surgical operation under circumstances of safety and good work efficiency.

However, the greatest of anxieties for achieving the requirements of items (1) and (2) is that the surgical operation under the endoscope becomes difficult because of a shortage in the amount of light.

As shown in FIG. 1, an illumination system of a rigid endoscope used for the surgical operation under the endoscope is provided with a light guide 1 on the scope side, receiving light emitted from a light source 8 to irradiate an observation part with the light. On the other hand, an observation system thereof includes an objective lens 2 receiving the light from the observation part to form an optical image, a relay lens 3 transmitting the optical image to an eyepiece section, and an eyepiece 4 for magnifying and observing the optical image transmitted by the relay lens 3.

The sectional area of the inserting section of the rigid endoscope is mostly occupied by the light guide 1 on the scope side and the relay lens 3. Thus, in order to diminish the diameter of the rigid endoscope, it is necessary to reduce the number of fibers of the light guide 1 on the scope side or diminish the outside diameter of the relay lens 3. However, a reduction in the number of fibers of the light guide 1 on the scope side causes the amount of light for irradiating the observation part to be decreased, while diminishing the diameter of the relay lens 3 means that the amount of light received from the observation part is reduced.

Consequently, for example, when a rigid endoscope with an outside diameter of 10 mm is reduced to 3 mm, its sectional area is decreased to less than 10%, and thus the sum of the amount of light which can be transmitted by the light guide and that of the amount of light received by the observation system are also decreased at almost the same rate.

In the operating room for the exclusive use of the endoscope, the connecting light guide with as long as 10 m or more, extending from the light source to the operating table, is used to transmit the light. As such, with this connecting light guide, the amount of light is diminished to less than 30% because the light is absorbed by the material of fiber cores of the connecting light guide. Moreover, where the numerical aperture (NA) of the connecting light guide is low, a loss of the amount of light becomes more prominent. If the connecting light guide is a multi-fiber, the loss of the amount of light will be further caused at the entrance section of the light guide because the core share of the light guide is small.

SUMMARY OF THE INVENTION

It is, therefore, an object of the present invention to provide an illumination system which is adapted to solve the problem of the shortage of the amount of light which arises as to the whole of a small-diameter rigid endoscope system and an endoscope system in the operating room for the exclusive use of the endoscope.

In order to achieve this object, according to one aspect of the present invention, the illumination system for endoscope includes a light source device having an arc discharge lamp and a light source optical system, a light guide cable, and a rigid endoscope provided with a light guide on the scope side, using lenses as a relay optical system. The light source optical system projects the light-emitting section of the lamp on the entrance face of the light guide cable at a magnification of nearly 1×, and the light guide cable satisfies the following conditions:

$$0.25 \times Mg1^{1/2} < D_L/D_S < 0.5 \times Mg1^{1/2} \tag{1}$$

$$0.8 < Mg1 \times (D_C/D_L) < 1.2 \tag{2}$$

where $D_S$ is the outside diameter of the scope, $D_C$ is the diameter of the light guide cable, $D_L$ is the diameter of the light guide on the scope side, and Mg1 is the projection magnification of an optical element interposed between the light guide cable and the light guide on the scope side.

According to another aspect of the present invention, the illumination system for endoscope includes a light source device having an arc discharge lamp and a light source optical system, a light guide cable, and a rigid endoscope provided with a light guide on the scope side, using an image fiber as a relay optical system. The light source optical system projects the light-emitting section of the lamp on the entrance face of the light guide cable at a magnification of nearly 1×, and the light guide cable satisfies Condition (2) and the following condition:

$$0.4 \times Mg1^{1/2} < D_L/D_S < 0.6 \times Mg1^{1/2} \quad (3)$$

According to still another aspect of the present invention, the illumination system for endoscope includes a light source device having an arc discharge lamp and a light source optical system, a light guide cable of a single fiber, and a rigid endoscope provided with a light guide on the scope side. The light source optical system projects the light-emitting section of the lamp on the entrance face of the light guide cable of a single fiber at a magnification of nearly 1×, and the light guide cable of a single fiber satisfies the following conditions:

$$D_L/D_S < 0.4 \times Mg1 \quad (4)$$

$$Mg1 \times D_C < D_L \quad (5)$$

According to a further aspect of the present invention, the illumination system for endoscopes includes at least one light source device using an arc discharge lamp, a connecting light guide whose entrance end is branched in accordance with the number of light source devices, and a connecting optical system for rendering light emerging from the connecting light guide incident on the entrance end of a light guide cable. The illumination system satisfies the following conditions:

$$NA2 > NA1 \quad (6)$$

$$0.8 < (NA2/NA1) \times Mg2 < 1.2 \quad (7)$$

where NA1 is the numerical aperture of the connecting light guide, Mg2 is the projection magnification of the connecting optical system, and NA2 is the numerical aperture of the light guide cable.

This and other objects as well as the features and advantages of the present invention will become apparent from the following detailed description of the preferred embodiments when taken in conjunction with the accompanying drawings.

DETAILED DESCRIPTION OF THE PREFERRED EMBODIMENTS

The embodiments of the present invention will be explained below.

First Embodiment

Figure 1:
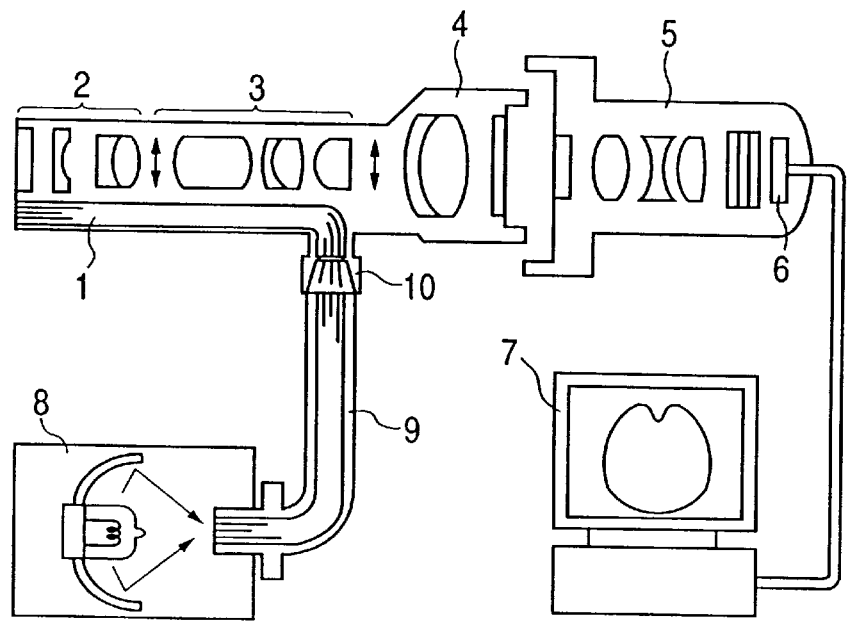
FIG. 1 is a schematic view showing the whole of a rigid endoscope system.

In the first embodiment, a description is given of the illumination system for obtaining sufficient brightness in a small-diameter rigid endoscope. As seen from the rigid endoscope system shown in FIG. 1, in the surgical operation under the endoscope at present, an optical adapter 5 is attached to an eyepiece section including the eyepiece 4 of the rigid endoscope so that an image is received by a CCD 6, and an operator performs manipulation while observing the image on a TV monitor 7.

In the illumination system of the rigid endoscope, light emitted from the light source 8 is transmitted to the entrance section of the light guide 1 on the scope side by a light guide cable 9. Also, the light guide cable 9 is connected directly or through an optical element 10 (for example, a lens or a conical fiber) for converting the NA of transmission light with the light guide 1 on the scope side. The light incident upon the light guide 1 on the scope side is transmitted to the distal end of the scope to irradiate an object.

In the observation optical system of the rigid endoscope, on the other hand, an image formed by the objective lens 2 is sent by the relay lens 3 and is magnified by the eyepiece 4. The brightness of the observation optical system is governed by the NA on the exit side of the relay lens 3 and the magnification of the eyepiece 4. In general, the NA on the exit side and the size of the image after the transmission of the image by the relay lens are proportional to the diameter of the relay lens. In addition, when the diameter of the relay lens is enlarged, the size of the image to be relayed, as well as the F-number of the lens, increases in proportion to the diameter of the lens. As such, it is generally known that the brightness of the observation optical system in the rigid endoscope is roughly proportional to the fourth power of the diameter of the relay lens 3.

In order to reduce the outside diameter of the rigid endoscope, it is necessary to achieve this purpose without decreasing the amount of transmission light of the light guide transmitting irradiation light. In the first embodiment, a xenon light source is used as the light source 8 in order to obtain a large amount of light in a small-diameter light guide. This xenon light source employs a superhigh luminance xenon lamp with a power consumption of 400 W and incorporates an optical system most suitable for the small-diameter light guide, as described below.

Figure 2:
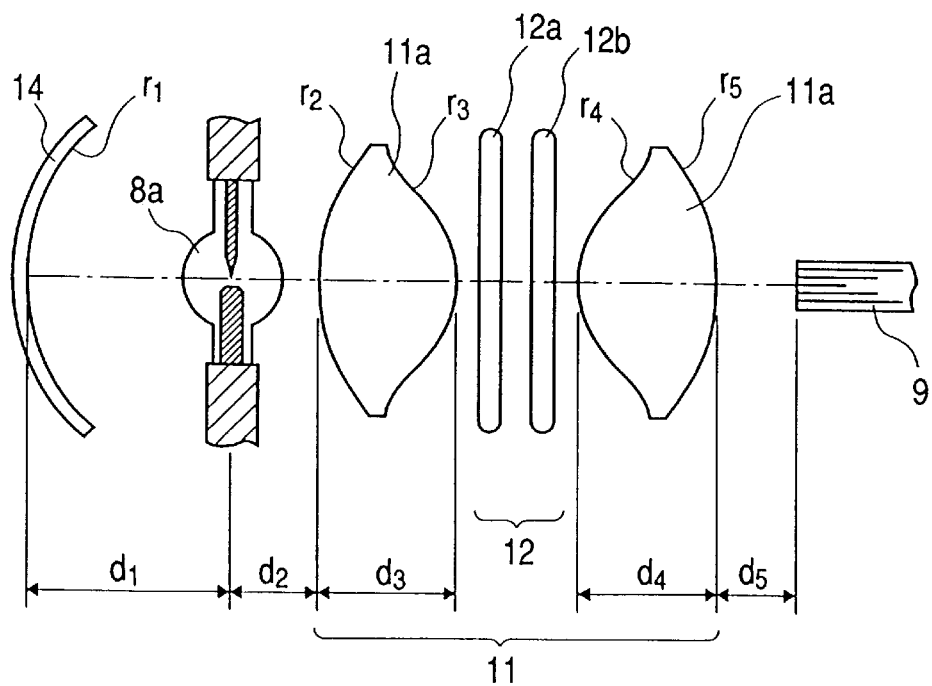
FIG. 2 is a schematic view showing a light source device in a first embodiment of the illumination system for endoscopes according to the present invention.

The light source device in the first embodiment, as shown in FIG. 2, the arc axis of a xenon lamp 8a is placed to be normal to the optical axis. Moreover, a light source optical system 11 for forming an image at about 1× magnification is interposed between the xenon lamp 8a and the light guide cable 9, and thereby the image of the light-emitting section of the xenon lamp 8a is projected on the end face of the light guide cable 9.

The light source optical system 11 used in the first embodiment is favorably corrected for aberration by using two aspherical lenses 11a, so that light is efficiently collected on the end face of the light guide cable 9. The lenses 11a are arranged to be practically afocal therebetween, and two filters 12 for removing infrared rays are interposed between the lenses 11a. These filters 12 are composed of an infrared reflecting filter 12a using an interference film to reflect infrared rays and an infrared absorbing filter 12b for absorbing infrared rays. By combining these filters, infrared rays emitted from the xenon lamp 8a are almost completely removed.

A spherical mirror 14 is disposed on the opposite side of the light guide cable 9, with its center of curvature at the light-emitting section of the lamp 8a. In this way, a beam of light emitted from the lamp 8a toward the spherical mirror 14 is reflected by the spherical mirror 14, and an image is formed at the original position of the light-emitting section. Thus, a luminance image of luminance about twice the emission luminance of the xenon lamp 8a is formed through the optical system 11 on the end face of the light guide cable 9.

Figure 3:
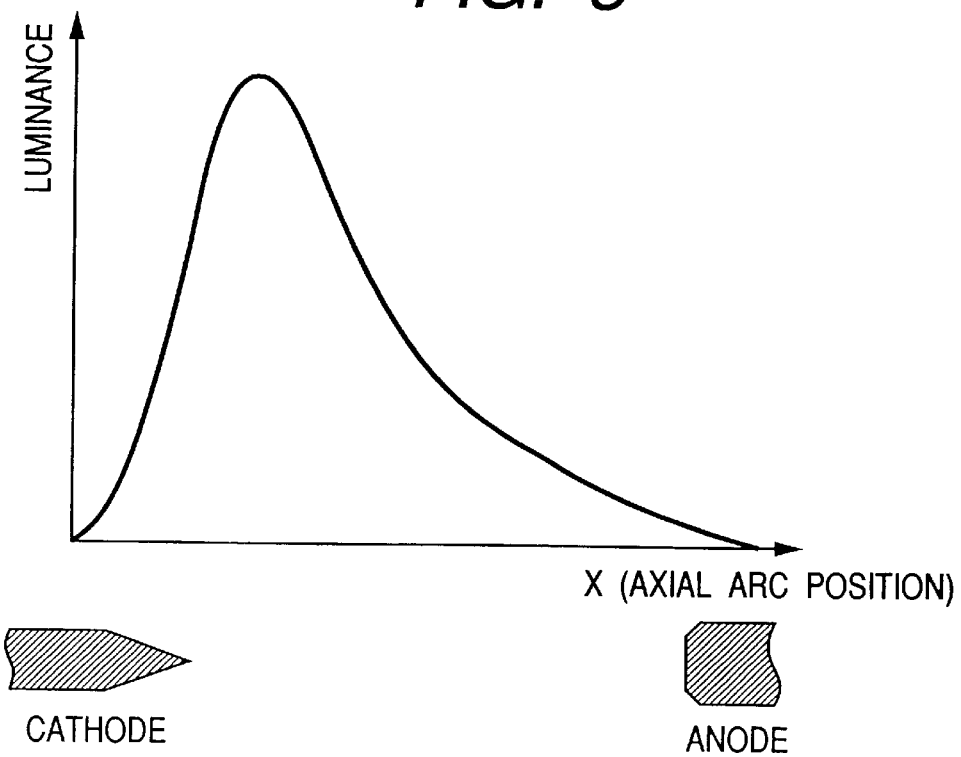
FIG. 3 is a graph showing a luminance distribution in the light-emitting section of a xenon lamp.

As seen from FIG. 3, the luminance distribution of the arc discharge lamp, such as a xenon lamp or a metal halide lamp, is very wide. The light source optical system used in the first embodiment has the projection magnification of approximately 1× and is favorably corrected for aberration, and the luminance image projected on the end face of the light guide cable has almost the same distribution as in FIG. 3.

As mentioned above, the light source device in the first embodiment uses the superhigh luminance xenon lamp. Moreover, the optical system with about 1× magnification which is favorably corrected for aberration projects a minute light-emitting section on the end face of the light guide cable, and is combined with the reflecting mirror, thereby doubling the luminance. Consequently, even when the light guide cable is a small-diameter light guide, a considerable amount of light can be rendered incident thereon. The use of the light source device most suitable for the small-diameter light guide allows the amount of light which is equal to or larger than that of a large-diameter light guide cable of a conventional light source device to be incident on the small-diameter light guide.

Figure 4:
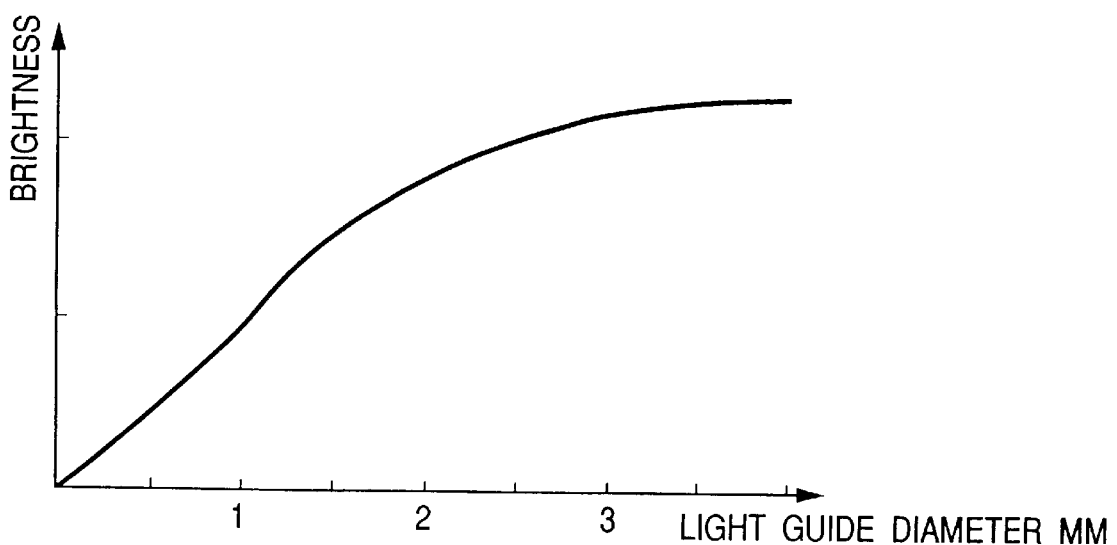
FIG. 4 is a graph showing the relationship between the diameter of a light guide and the amount of light of a light source device in the first embodiment.
Figure 5:
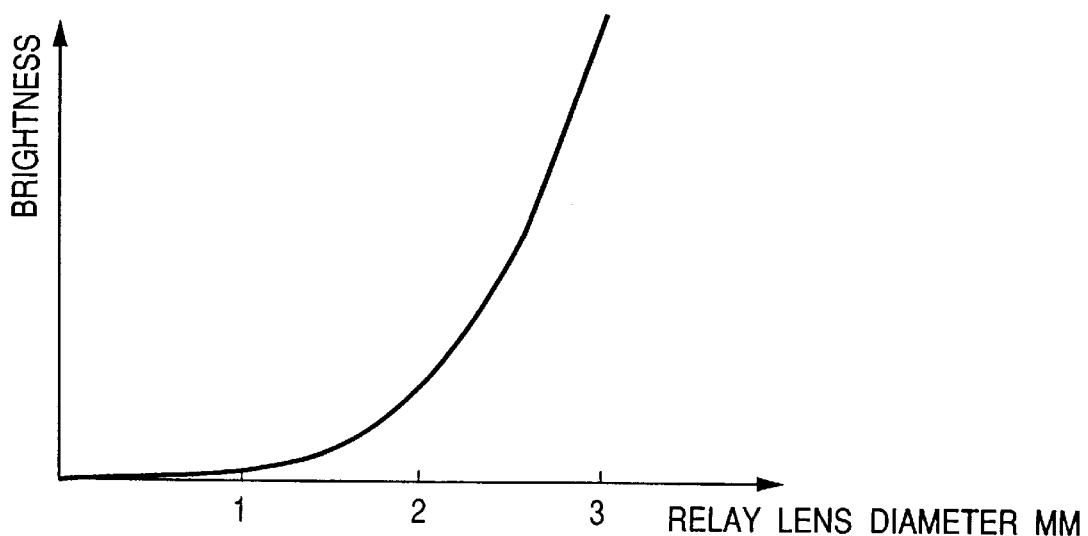
FIG. 5 is a graph showing the relationship between the diameter of a relay lens and the amount of light of a rigid endoscope.
Figure 6:
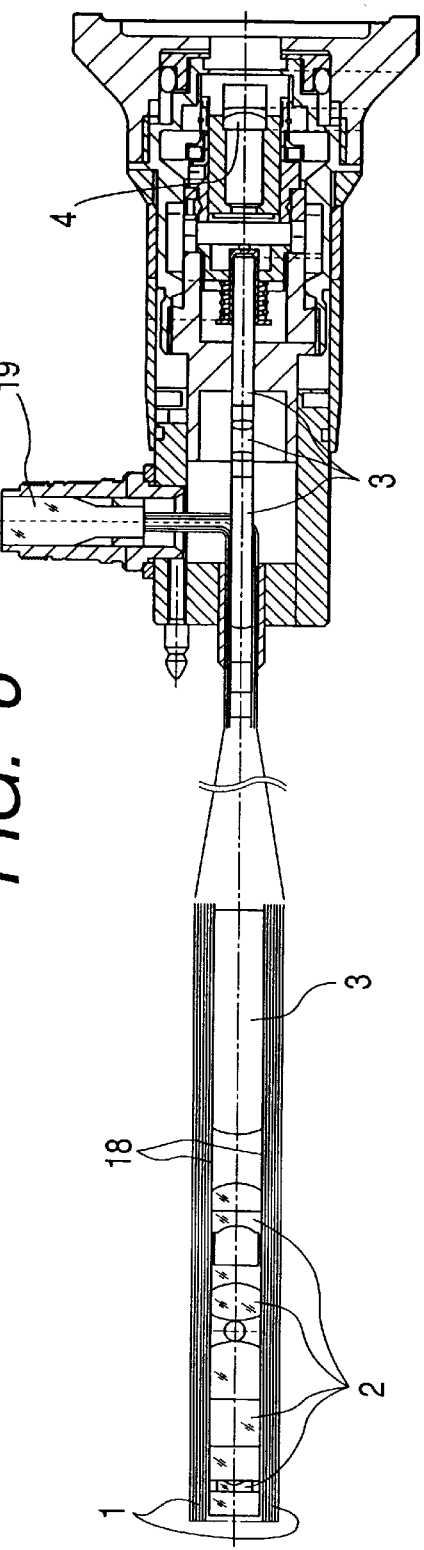
FIG. 6 is a sectional view showing a rigid endoscope using a relay lens and a conical fiber in an observation optical system.

FIG. 4 shows the relationship between the diameter of the light guide cable and the amount of light of the light source device in the first embodiment. As mentioned above, the amount of transmission light of the relay lens of the rigid endoscope is proportional to the fourth power of the diameter of the lens. In FIG. 5, the relationship between the diameter of the relay lens and the amount of light is shown. The rigid endoscope used in the first embodiment is shown in FIG. 6.

In the rigid endoscope, the sectional area of the scope is mainly occupied by the objective lens 2 or the relay lens 3 and the light guide 1 on the scope side, and brightness obtained by the entire rigid endoscope system is found from the graphs of FIGS. 4 and 5 in accordance with the diameter of the rigid endoscope.

Figure 7:
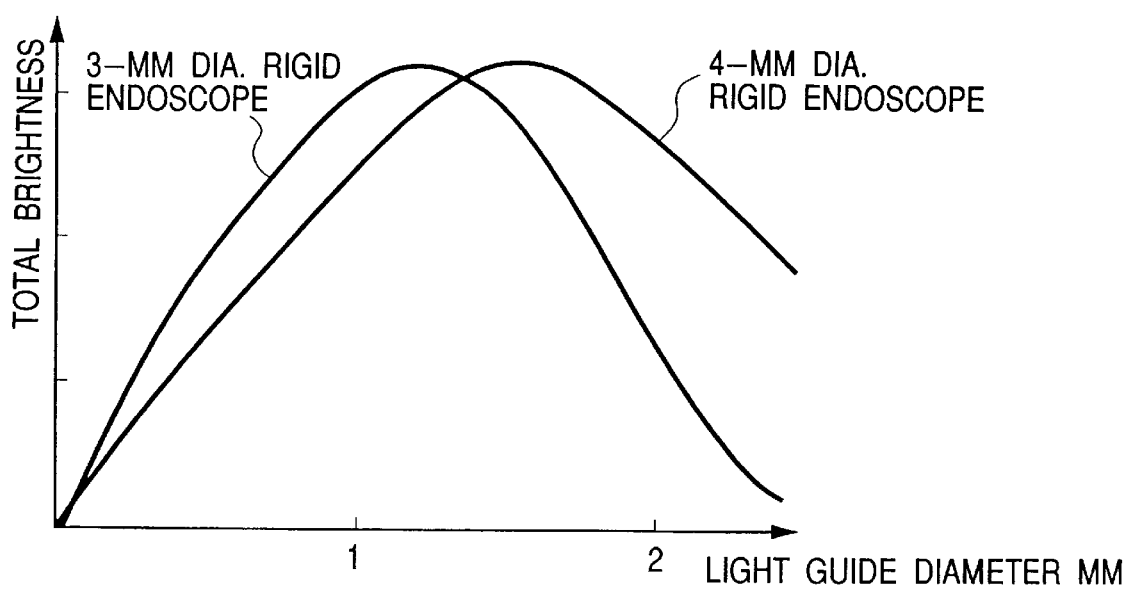
FIG. 7 is a graph showing the brightness of rigid endoscope systems with different diameters.

FIG. 7 shows the brightness of the entire rigid endoscope system in the case where each of rigid endoscopes with diameters of 3 and 4 mm is combined with the light source device of the first embodiment. In the graph of FIG. 7, the total brightness is plotted along the axis of ordinates and the diameter of the light guide on the scope side along the axis of abscissas. The maxima of brightness are normalized to be identical. In this case, the thickness of a pipe 18 in which the relay lens is encased can be as thin as 0.1 mm, so that the maximum brightness is obtained with respect to the diameter of the light guide 1 on the scope side.

As seen from FIG. 7, when the rigid endoscope is combined with the light source device of the first embodiment which is most suitable for the small-diameter light guide, an appreciably satisfactory amount of light is obtained by setting the diameter of the light guide 1 on the scope side to about 35% of the outside diameter of each rigid endoscope, and a sufficient amount of light is obtained in the case of about 25–45%. Also, when the pipe 18 in which the relay lens 3 is encased has a thickness of 0.1 mm, the ratio between the diameters of the light guide 1 on the scope side and the relay lens is approximately 30–70%.

As such, a sufficient amount of light can be obtained even with a small-diameter rigid endoscope when the outside diameter $D_S$ of the scope and the diameter $D_L$ of the light guide on the scope side of the rigid endoscope combined with the light source device in the first embodiment satisfy the following condition:

$$0.25 < D_L/D_S < 0.5 \qquad (8)$$

In the graph of FIG. 7, the light guide cable and the light guide on the scope side have identical diameters and are directly connected, without interposing the optical element therebetween, so that the loss of the amount of light is minimized. In practical use, however, almost the same amount of light is obtained when the diameter $D_C$ of the light guide cable and the diameter $D_L$ of the light guide on the scope side practically satisfy the following condition:

$$0.8 < D_C/D_L < 1.2 \qquad (9)$$

In this case, the relationship between a diameter $D_R$ of the relay lens and the diameter $D_L$ of the light guide on the scope side is given by $$0.3 < D_L/D_R < 0.7 \qquad (10)$$

In this way, Condition (10) is set so that Conditions (8) and (9) are satisfied and in addition, the maximum amount of light is obtained.

Figure 8A:
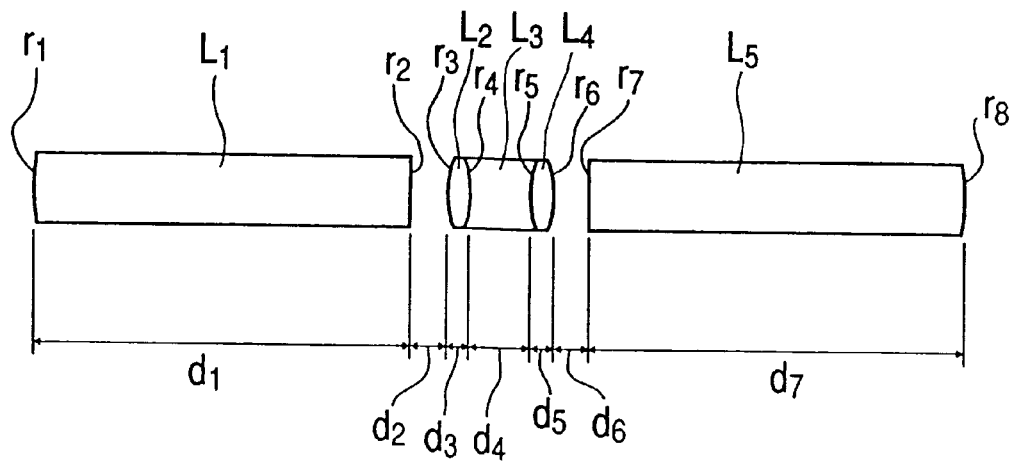
FIGS. 8A and 8B are schematic views showing examples of arrangements of relay lenses in rigid endoscopes with different outside diameters.
Figure 8B:
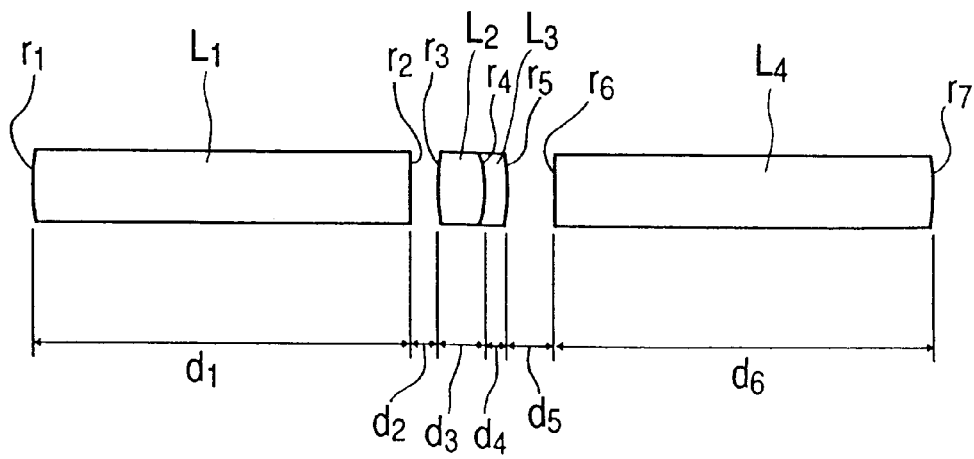

FIGS. 8A and 8B show examples of setting values of the diameters of the relay lenses and the light guides on the scope side of rigid endoscopes with outside diameters of 3 and 4 mm, respectively, which satisfy Condition (10), and the arrangements of the relay lenses. The scope shown in each of these examples satisfy Conditions (8) and (10) and is capable of obtaining a sufficient amount of light by combining the light guide satisfying Condition (9) with the light source device suitable for the small-diameter light guide.

For the small-diameter rigid endoscope, in order to diminish the outside diameter of the rigid endoscope, it is necessary to reduce even the thickness of the pipe 18 in which the relay lens 3 is encased. In each of the examples shown in FIGS. 8A and 8B, the thickness of the pipe is set to 0.1 mm. In the present invention, however, a sufficient amount of light is obtained even with the small-diameter light guide, and thus the rigid endoscope system can also be designed so that not only is brightness improved, but also strength is increased by setting the pipe thickness to at least 0.15 mm.

In the above description, the light guide cable and light guide on the scope side have identical NAs and are directly connected without placing the optical element at a connection therebetween. For a rigid endoscope with a wide angle of field, however, it is necessary to increase the NA of the light guide on the scope side and provide light incident on this light guide with high NA.

In such a rigid endoscope with a wide angle of field, it is common practice to provide the entrance section of the light guide on the scope side with a conical fiber 19 and thereby to obtain the high NA. By the conical fiber 19, the image of the exit end face of the light guide cable is demagnified and projected on the end face of the light guide on the scope side. Hence, where the conical fiber is used, the diameter of the light guide on the scope side is substantially reduced, and accounts for a small proportion of the outside diameter of the scope.

Figure 9A:
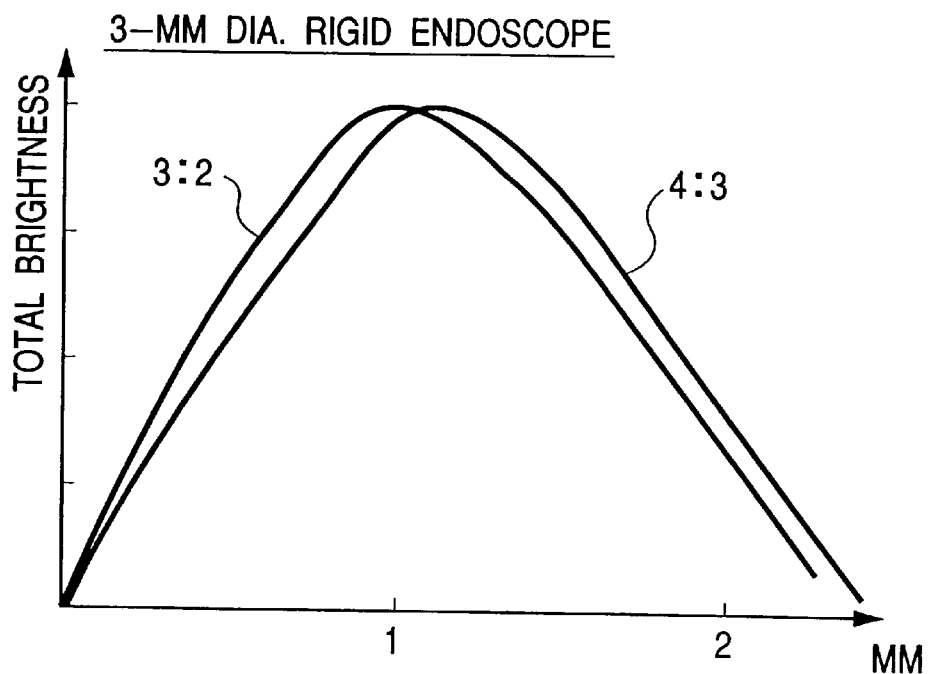
FIGS. 9A and 9B are graphs each showing the total brightness of the illumination system for endoscopes using a conical fiber which is different in the ratio between the diameters of the entrance end and the exit end thereof.
Figure 9B:
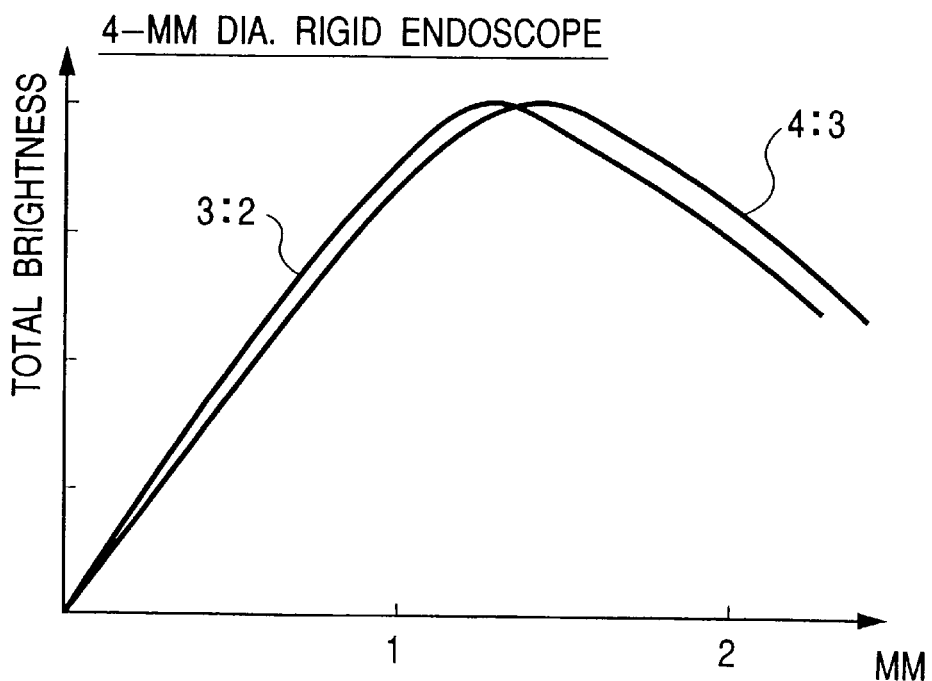

FIGS. 9A and 9B illustrate the brightness of the entire systems where rigid endoscopes have outside diameters of 3 and 4 mm, respectively, using conical fibers in which the ratios between the diameters of the entrance end and the exit end are 4:3 and 3:2. In the graphs of these figures, the maxima of brightness are normalized to be identical. Also, the diameter of the light guide cable combined in this case is equal to a value obtained by multiplying the diameter of the light guide on the scope side by the reciprocal of the ratio of reduction of the conical fiber.

It is seen from each of the graphs that the diameter of the light guide on the scope side which brings about the best brightness of the entire system in this case is nearly equal to the half power of the ratio of reduction of the conical fiber in either of the rigid endoscopes. Thus, where the conical fiber is interposed between the light guide cable and the light guide on the scope side, Condition (8) is substituted by Condition (1). In this case, however, Mg1 of Condition (1) denotes the demagnifying of the conical fiber. The use of an optical element other than the conical fiber brings about the same effect even at the high NA, and if Condition (1) is satisfied when the demagnifying of the optical element is represented by Mg1, a sufficient amount of light can be obtained.

Also, for the light guide cable combined in this case, the maximum amount of light is obtained by using the light guide cable with the diameter of a value derived when the diameter of the light guide on the scope side is multiplied by the reciprocal of the ratio of reduction of the conical fiber. In practice, however, when the diameter of the light guide cable is ±20% of this value, no appreciable amount of light is reduced. Hence, the diameter of the light guide cable combined in this case is defined by Condition (2). Similarly, Condition (10) can be expressed by $$0.3 \times Mg1^{1/2} < D_L/D_R < 0.7 \times Mg1^{1/2} \qquad (11)$$

Figure 10:
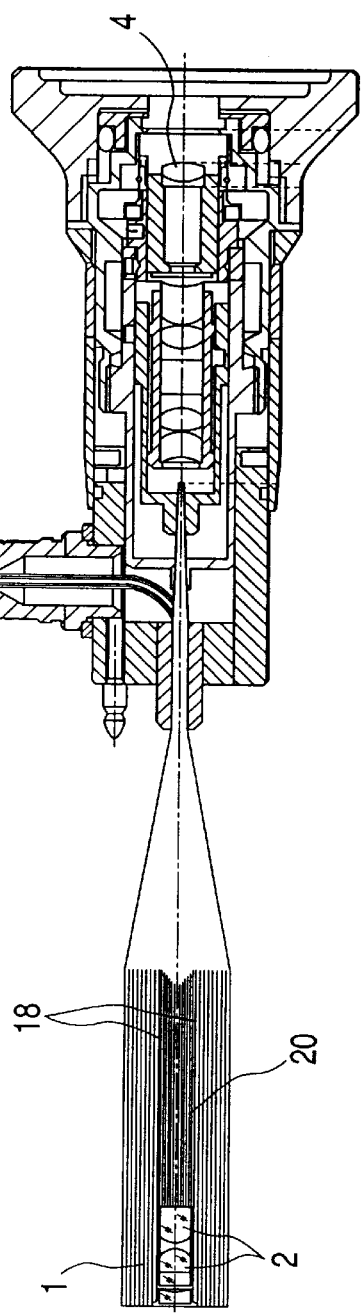
FIG. 10 is a sectional view showing a small-diameter rigid endoscope using an image fiber in the observation optical system.

Some of small-diameter rigid endoscopes use not relay lenses but image fibers in the observation optical systems. An example of such a rigid endoscope is shown in FIG. 10. In the rigid endoscope using an image fiber bundle 20, even through the number of fibers in the image fiber bundle is increased to enlarge the diameter of the bundle, the NA of the image fiber bundle will not be increased, and thus only the enlargement of a transmission area affects brightness.

In this way, with the small-diameter rigid endoscope using the image fiber bundle, the brightness of the observation optical system is proportional to the square of the diameter of the fiber bundle. Consequently, the rigid endoscope using the image fiber bundle has a tendency that the diameter of the light guide (on the scope side) bringing about the maximum amount of light becomes large compared with the relay lens type rigid endoscope in which the brightness of the observation optical system is proportional to the fourth power of the diameter of the relay lens.

Figure 11:
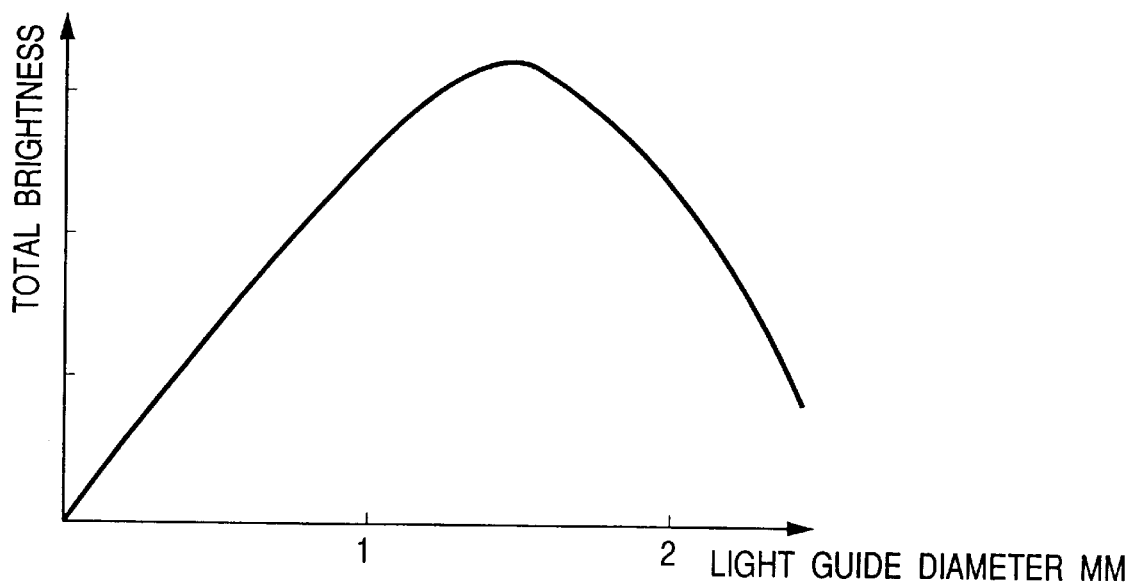
FIG. 11 is a graph showing the relationship between the diameter of the light guide and the amount of light.

FIG. 11 illustrates the brightness of the entire system where the rigid endoscope with an outside diameter of 3 mm, using the image fiber bundle, is combined with the light source device in the first embodiment. As seen from the graph of this figure, in the rigid endoscope using the image fiber bundle, the maximum amount of light is obtained when the diameter of the light guide accounts for about 50% of the outside diameter of the scope, and sufficient brightness is obtained when these diameters satisfy the following condition:

$$0.4 < D_L/D_S < 0.6 \qquad (12)$$

In this case, the diameter of the light guide cable is set by Condition (9) as in the case where the relay lens is used.

Also, in the rigid endoscope using the image fiber bundle, the outside diameter $D_R$ of the image fiber bundle used as the relay optical system and the diameter $D_L$ of the light guide on the scope side, like Condition (10), have the following relation:

$$0.5 < D_L/D_R < 0.9 \qquad (13)$$

Moreover, the pipe 18 in which the image fiber bundle is encased is designed to have a thickness of at least 0.15 mm for the scope of high strength.

When the connection of the light guide is provided with the optical element converting the NA, such as the conical fiber 19, the rigid endoscope system satisfies Conditions (2) and (3) and the following condition:

$$0.5 \times Mg1^{1/2} < D_L/D_R < 0.9 \times Mg1^{1/2} \qquad (14)$$

As mentioned above, the light source device is combined with the illumination system peculiarly suitable for the small-diameter rigid endoscope, and thereby even the small-diameter rigid endoscope, for example, as small as 3 or 4 mm in outside diameter, is capable of obtaining brightness sufficient for performance of the surgical operation under the endoscope.

The use of a single fiber (a single optical fiber) for the light guide cable is very advantageous for the acquisition of the amount of light because a fiber core accounts for 100% of the sectional area of the fiber. In this case, however, there is a limit to the diameter of the light guide cable (here, the diameter of the single fiber) in view of its hardness and bending. Consequently, when the single fiber is used for the light guide cable, the design of the rigid endoscope system is different from the case where the diameter of the light guide cable can be ideally set as mentioned above.

Where the single fiber is used for the light guide cable, a fiber with a diameter of about 0.5 mm has practical use in view of the hardness and bending, and about 0.8 mm at a maximum. Hence, in the use of the single fiber, it is impossible to enlarge the diameter of the light guide cable in accordance with a necessary amount of light. In the case of the single fiber, however, the core share of the fiber is 100% and thus the amount of light about twice that of a multi-fiber of identical diameter can be obtained.

As seen from the graph of FIG. 4, a 0.5-mm-diameter single fiber is capable of obtaining the amount of light equivalent to a 1.0-mm-diameter multi-fiber, and a 0.8-mm-diameter single fiber to a 1.5-mm-diameter multi-fiber. As such, when a single-fiber light guide cable is used, the same amount of light is obtained with about half of the diameter of a multi-fiber light guide cable, and the diameter of the relay optical system can be enlarged accordingly. The amount of light of the entire system can thus be further increased. In this way, when the single-fiber light guide cable is used in the rigid endoscope system, the diameter of the light guide cable used diminishes and the light guide accounts for a small proportion of the sectional area of the rigid endoscope.

Thus, a large amount of light can be obtained in the entire system when the ratio of the diameter $D_L$ of the light guide to the outside diameter $D_S$ of the scope in the rigid endoscope combined with the light source device according to the present invention is below 40%:

$$D_L/D_S < 0.4 \qquad (15)$$

In the single-fiber light guide cable, as mentioned above, the same amount of light is obtained with about half of the diameter of the multi-fiber light guide cable. Thus, if the diameter of the light guide on the scope side is set to be somewhat larger than that of the single-fiber light guide cable so that light is positively received, sufficient brightness can be obtained in the entire system.

Consequently, the relation between the diameter $D_C$ of the light guide cable and the diameter $D_L$ of the light guide on the scope side is as follows:

$$D_C < D_L \qquad (16)$$

Where the relay optical system is used, the proportion of the relay optical system to the entire rigid endoscope further increases, and hence, as in Condition (10), the relation between the outside diameter $D_R$ of the relay optical system and the diameter $D_L$ of the light guide on the scope side is given by $$0.1 < D_L/D_R < 0.5 \qquad (17)$$

When the optical element for converting the NA, such as the conical fiber, is placed at the connection of the light guide as described above, the corresponding diameters satisfy Conditions (4) and (5) and the following condition:

$$0.1 \times Mg1^{1/2} < D_L/D_R < 0.5 \times Mg1^{1/2} \qquad (18)$$

Lens data used in the first embodiment are listed below.

(Refer to FIG. 2)

$d_1 = 30$, $d_2 = 11.8$, $d_3 = 21$, $d_4 = 21$, $d_5 = 11.8$
$r_1 = 30$, $r_2 = 32.025$, $r_3 = \infty$ (aspherical), $r_4 = \infty$ (aspherical),
$r_5 = -32.025$
Spherical lenses 11
$D = 42$, $n = 1.5231$, $\nu = 58.49$
Conic constants and aspherical coefficients Third surface $C = 0$, $P = 0$
$B = -3.6 \times 10^{-2}$,   $E = 4.4557 \times 10^{-7}$,
$F = -8.1291 \times 10^{-9}$,   $G = 1.1544 \times 10^{-10}$,
$H = -7.086 \times 10^{-17}$,   $I = -8.9393 \times 10^{-17}$ Fourth surface $C = 0$, $P = 0$
$B = 3.6 \times 10^{-2}$,   $E = -4.4557 \times 10^{-7}$,
$F = 8.1291 \times 10^{-9}$,   $G = -1.1544 \times 10^{-10}$,
$H = 7.086 \times 10^{-17}$,   $I = 8.9393 \times 10^{-17}$ (Refer to FIG. 8A)

$d_1 = 14.85$, $d_2 = 1.522$, $d_3 = 0.83$, $d_4 = 2.35$, $d_5 = 0.83$, $d_6 = 1.522$, $d_7 = 14.85$
$r_1 = 7.204$, $r_2 = \infty$, $r_3 = 5.355$, $r_4 = -3.364$, $r_5 = 3.364$, $r_6 = -5.355$, $r_7 = \infty$, $r_8 = -7.204$
First lens $L_1$   $n_1 = 1.5891$, $\nu_1 = 61.18$
Second lens $L_2$   $n_2 = 1.6127$, $\nu_2 = 58.75$
Third lens $L_3$   $n_3 = 1.7880$, $\nu_3 = 47.38$
Fourth lens $L_4$   $n_4 = 1.6127$, $\nu_4 = 58.75$
Fifth lens $L_5$   $n_5 = 1.5891$, $\nu_5 = 61.18$ (Refer to FIG. 8B)

Figure 12:
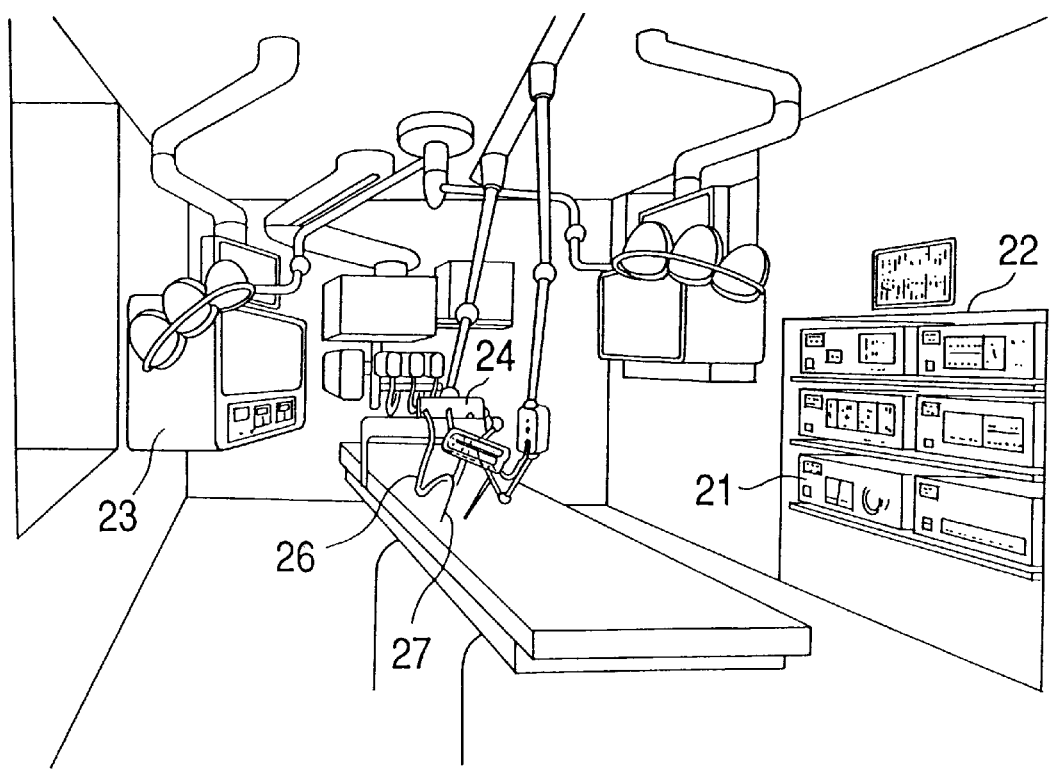
FIG. 12 is a schematic view showing the appearance of an operating room for the exclusive use of the endoscope.

$d_1 = 21.33$, $d_2 = 1.5$, $d_3 = 2.76$, $d_4 = 1.24$, $d_5 = 2.54$, $d_6 = 21.33$
$r_1 = 10.236$, $r_2 = \infty$, $r_3 = 17.896$, $r_4 = -3.399$, $r_5 = -8.773$, $r_6 = \infty$, $r_7 = -10.236$
First lens $L_1$   $n_1 = 1.6200$, $\nu_1 = 36.26$
Second lens $L_2$   $n_2 = 1.6237$, $\nu_2 = 47.10$
Third lens $L_3$   $n_3 = 1.7174$, $\nu_3 = 29.51$
Fourth lens $L_4$   $n_4 = 1.6200$, $\nu_4 = 36.26$ Second Embodiment The illumination system of the operating room for the exclusive use of the endoscope is shown as the second embodiment. The operating room for the exclusive use of the endoscope in this embodiment, as illustrated in FIG. 12, is equipped with an instrument housing section 22 incorporating instruments used for the surgical operation, including a light source 21, in the wall of the operating room. A monitor 23 for displaying a scope image the operator observes and a connector unit 24 are suspended from the ceiling of the operating room.

Light emitted from the light source 21 incorporated in the instrument housing section 22 is transmitted to the connector unit 24 by a light guide cable connected through the wall and a ceiling 25. The connector unit 24 functions as a secondary light source. When a source plug 26 of the light guide on the scope is thus connected to the connector unit 24, the amount of light necessary for a scope 27 is supplied.

Figure 13:
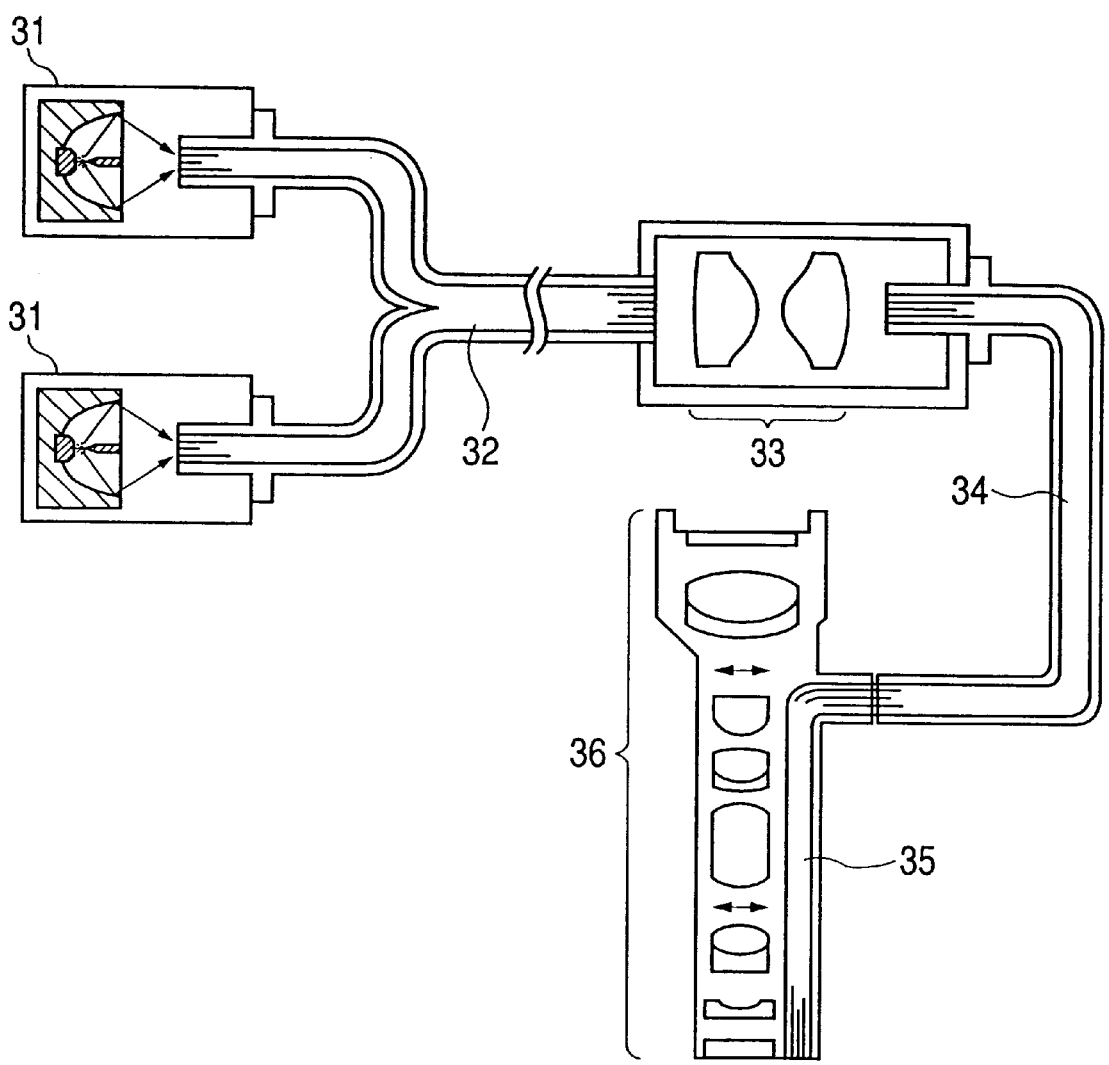
FIG. 13 is a schematic view showing the construction of an illumination system for the operating room for the exclusive use of the endoscope in a second embodiment of the illumination system for endoscopes according to the present invention.

The illumination system in the second embodiment, as shown in FIG. 13, uses two xenon light sources 31, and light emitted from the two light sources 31 is transmitted, through a two-branched, connecting light guide 32, to the entrance section of a light guide 35 on the scope side. In this case, the light emerging from the connecting light guide 32 is optically connected to the entrance end of a light guide cable 34 by a connecting optical system 33.

In the case of the rigid endoscope, as stated in the first embodiment, it is common practice that the light guide is divided on the scope side, so that the light is rendered incident upon the light guide on the scope side through the light guide cable 34. Thus, in the second embodiment, the system of a rigid endoscope 36 using the light guide cable 34 on the way to the transmission of the light is explained as an example.

As mentioned above, the greatest anxiety in the second embodiment is that the loss of the amount of light is caused by the connecting light guide with a length of 10 m or more and the amount of light necessary for the surgical operation under the endoscope is not obtained.

Figure 14A:
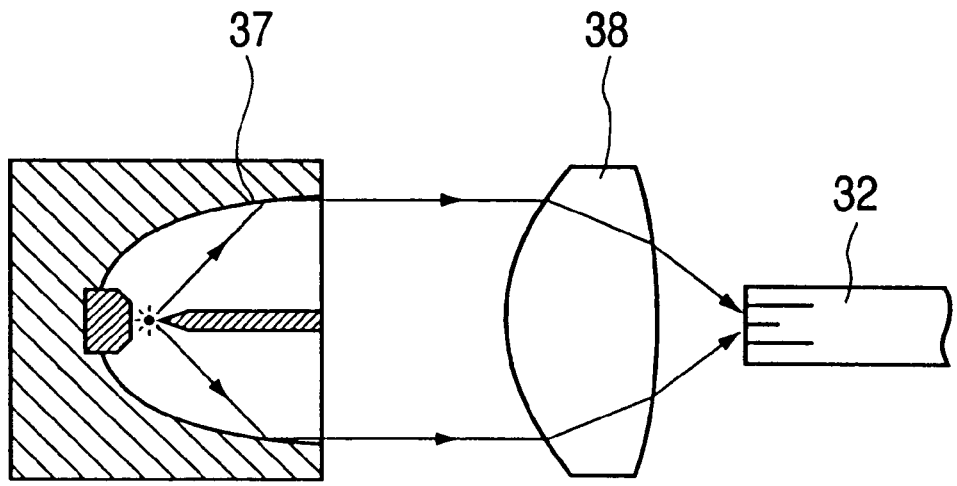
FIGS. 14A and 14B are schematic views showing ways of collecting a light beam on the end face of the light guide.
Figure 14B:
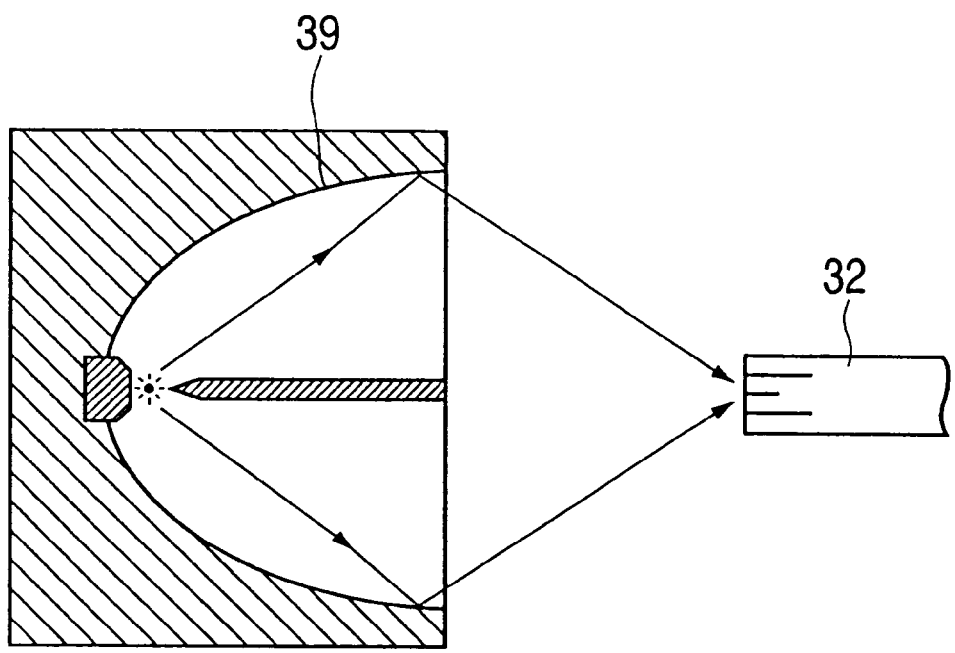

Components required to solve the problem of the loss of the amount of light will be described in detail below. When the xenon lamp is used in each of the light sources, as shown in FIG. 14A, it is common practice to collect a light beam on the end face of the connecting light guide 32 by using a parabolic mirror 37 and a condenser lens 38, or as shown in FIG. 14B, by using an elliptical mirror 39. Also, the xenon lamp is such that light is emitted by the arc discharge of xenon gas and, in contrast with the halogen lamp, has a considerably high emission luminance and a wide distribution of emission luminance.

Figure 15A:
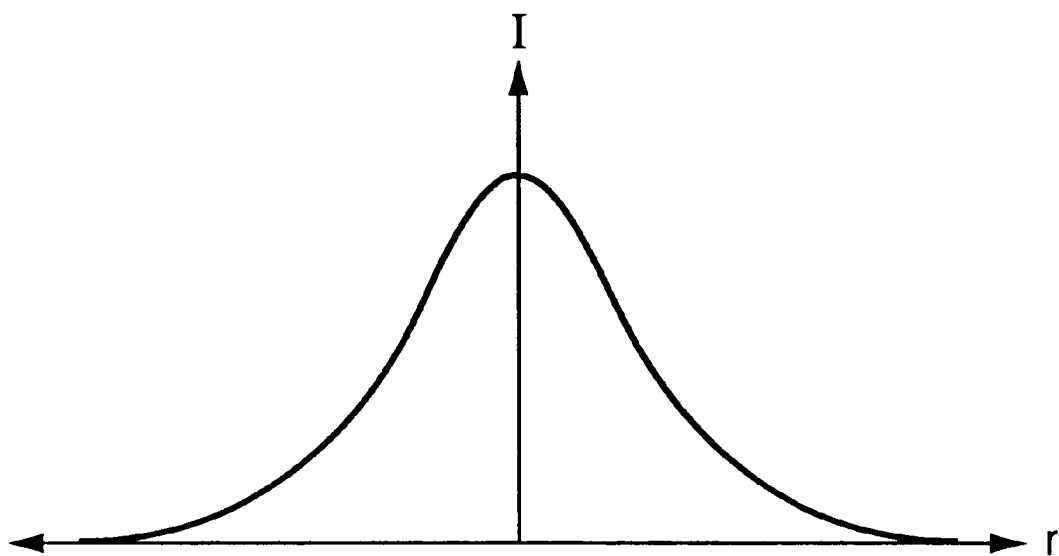
FIGS. 15A and 15B are graphs showing the intensity distribution of light collected on the end face of the light guide and the relationship between the diameter of the light guide and the amount of incident light, respectively.
Figure 15B:
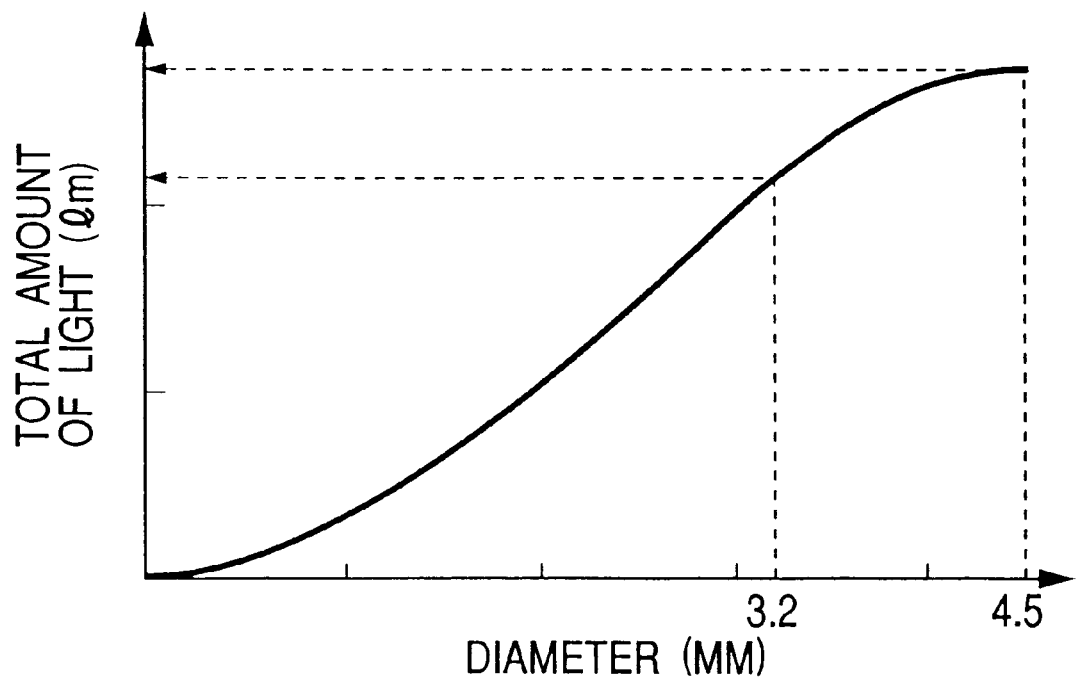

Consequently, the intensity distribution of light collected on the end face of the connecting light guide is as shown in FIG. 15A, and the relationship between the diameter of the connecting light guide and the amount of incident light is represented by a graph shown in FIG. 15B. As seen from the graph of FIG. 15B, when the light guide, for example, has a diameter of 4.5 mm and the entrance end of the light guide is branched into two so that entrance sections 3.2 mm in diameter are connected to individual light sources, the amount of light derived from the exit end of the light guide is at least 1.5 times as great as when an entrance section 4.5 mm in diameter is used.

In short, in order to avoid the loss of the amount of light caused by the connecting light guide as long as 10 m or more, two high-luminance xenon light sources are used and the entrance end of the connecting light guide is branched into two so that the amount of light is obtained from the two light sources. In this way, a sufficient amount of light is transmitted to the light guide on the scope.

The connecting light guide 32, with two branches 3.2 mm in diameter on the entrance side and a diameter of 4.5 mm on the exit side, has an NA of 0.5 and a transmittance as high as 99%/m. Moreover, this light guide is bundled so that the core share is more than 70%. In general, the NA of the light guide with high transmittance is low, and if an attempt is made to increase the NA of the light guide, the transmittance of core glass material will be reduced.

The connecting light guide 32 used in the second embodiment has an NA of 0.5, which is lower than an NA of 0.66 in the light guide cable 34. Hence, this light guide is great in loss of the NA, but because of its high transmittance, has the feature that there is essentially no loss due to the core glass material. The loss of the NA caused by the connecting light guide 32 can be recovered by the connecting optical system 33 optically connecting the connecting light guide 32 with the light guide cable 34.

Figure 16:
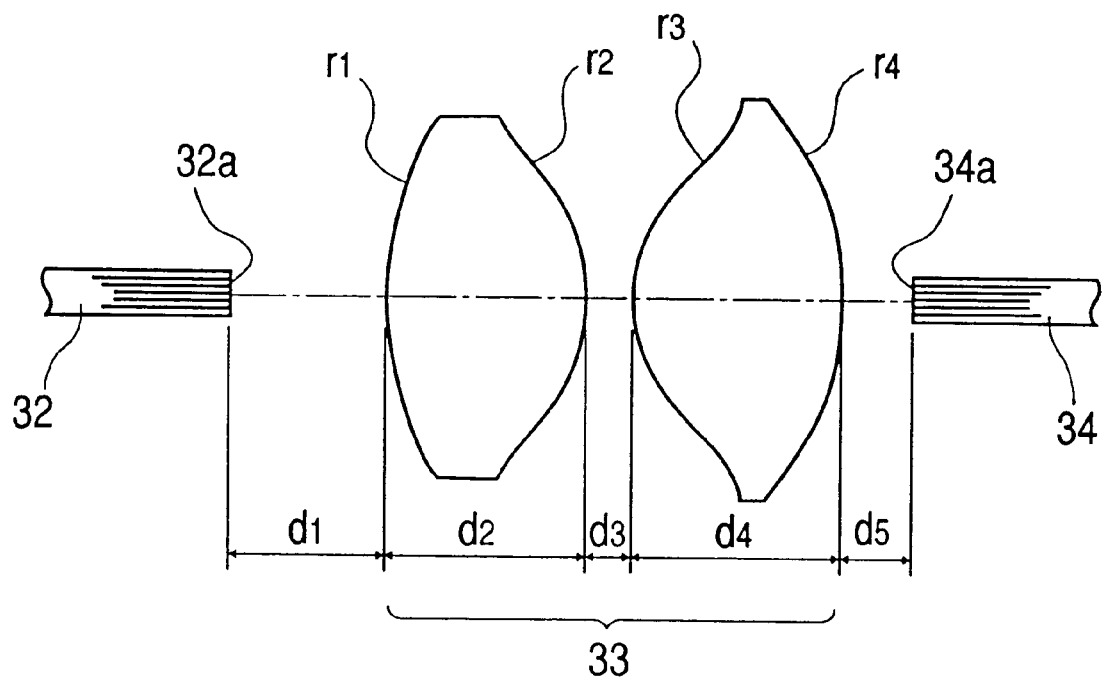
FIG. 16 is a view showing a connecting optical system in the second embodiment.

The NA of the connecting light guide 32 used in the second embodiment is 0.5, while that of the light guide cable 34 is 0.66. The connecting optical system 33 in the second embodiment, as shown in FIG. 16, is designed so that an exit end face 32a of the connecting light guide 32 is projected on an entrance end face 34a of the light guide cable 34. In this case, the paraxial magnification of the optical system is 0.77×, and the image of the end face is demagnified and projected.

In this way, although the NA is 0.5 on the exit end face 32a of the connecting light guide 32, it is changed to about 0.66 on the entrance end face 34a of the light guide cable 34 by the connecting optical system 33, and hence there is no loss of the amount of light due to an NA shortage. Furthermore, since the connecting optical system 33 in the second embodiment is favorably corrected for aberration by using two aspherical lenses, there is little loss of the amount of light due to the connecting optical system 33 and the light is efficiently incident on the light guide cable 34.

By constructing the illumination system as mentioned above, even when the light passes through the connecting light guide as long as 10 m or more, the amount of light can be obtained at almost the same level as the case of an operation under the conventional endoscope using the high-luminance xenon light source.

The light source device of the illumination system mentioned above is used to be most suitable for the light guide cable with an NA of 0.66 and is not necessarily efficient. Hence, the focal length of the optical system of the light source device is set according to the NA of the connecting light guide, and thereby the amount of light can be further increased.

Figure 17A:
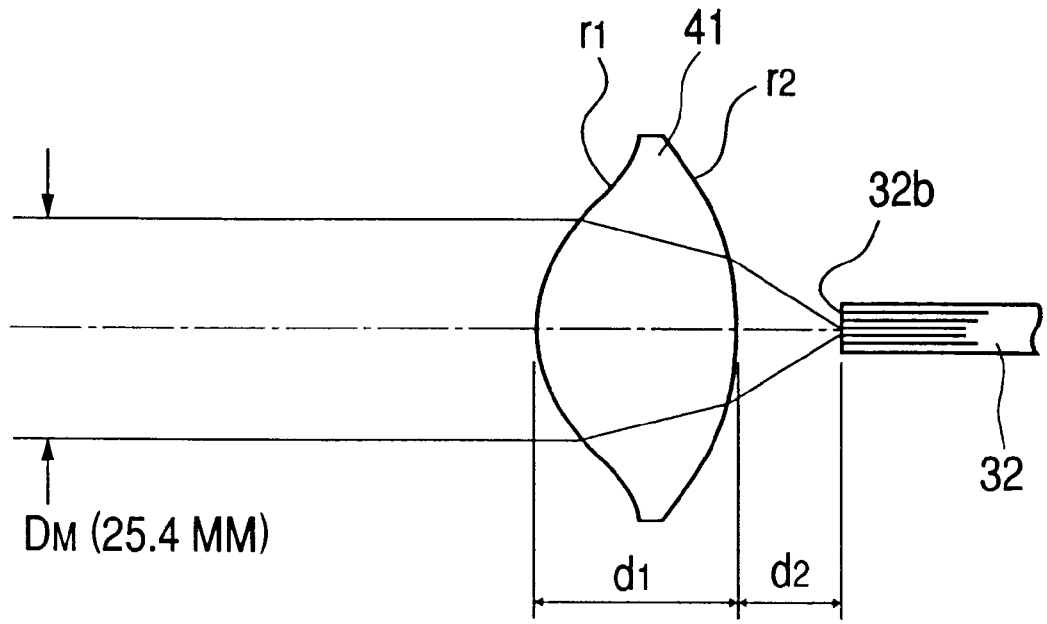
FIGS. 17A and 17B are schematic views showing the optical system of a conventional xenon light source and the optical system of a light source designed to accommodate the numerical aperture of the connecting light guide, respectively.
Figure 17B:
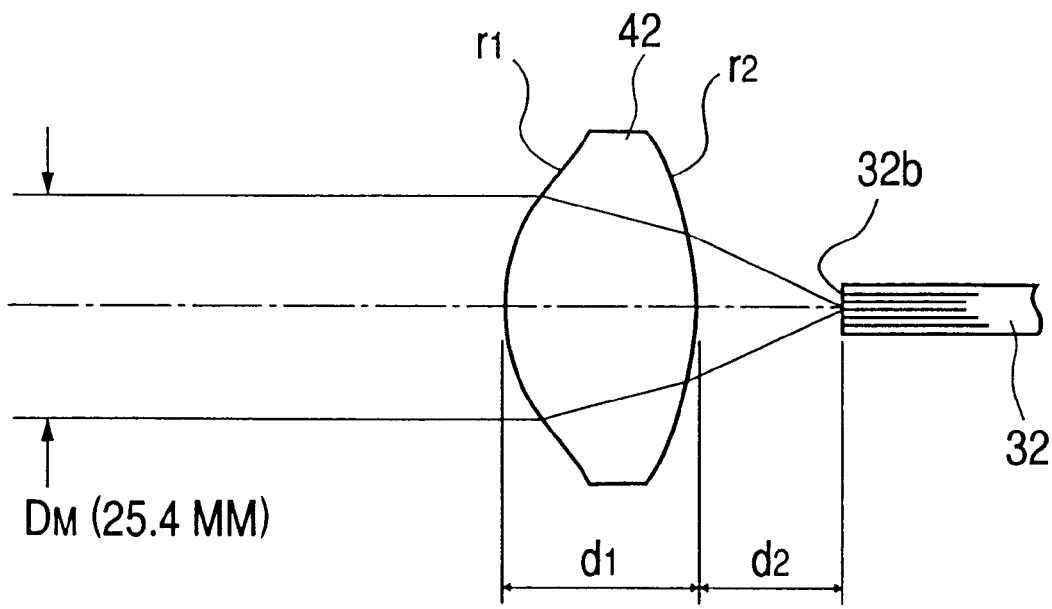

FIGS. 17A and 17B show the optical systems of a conventional xenon light source and a light source designed to accommodate the NA of the connecting light guide, respectively. Each of the optical systems uses the xenon lamp constructed integrally with a parabolic mirror to collect a parallel beam of light formed by the parabolic mirror on the end face of the connecting light guide through a condenser lens.

The focal length of a condenser lens 41 shown in FIG. 17A is 21.76 mm, while that of a condenser lens 42 in FIG. 17B is 24.98 mm. The size of the diameter of a converged spot can be enlarged in accordance with each focal length. In this case, the outside diameter of the condenser lens 42 shown in FIG. 17B is set so that an NA of at least 0.5 is obtained at an entrance end face 32b of the connecting light guide 32, and thus there is no loss of the amount of light due to the NA shortage.

When the arc discharge lamp, such as the xenon lamp, is used, as mentioned above, the intensity distribution at a light-collecting section is as shown in FIG. 15A. Therefore, unless the loss of the amount of light is caused by the NA shortage, the converged spot is enlarged and thereby the amount of light can be increased.

The NA of the light source optical system in the second embodiment is 0.5 which is substantially the same as that of the connecting light guide 32. Thus, the light source optical system is changed to that shown in FIG. 17B and thereby the amount of light, in contrast with the case of the conventional light source optical system of FIG. 17A, can be increased by about 20%. In this way, where the connecting light guide with high transmittance which is low in NA is used, it is advantageous for an increase of the amount of light to set the optical system on the source side so as to agree with the NA of the connecting light guide.

As mentioned above, when the focal length of the condenser lens on the source side is changed, the amount of light can be increased by about 20%, and even when the light passes through the connecting light guide as long as 10 m or more, the amount of light which is equivalent to or larger than that of the conventional case can be obtained.

Also, although the second embodiment uses two xenon light sources and the connecting light guide whose entrance end is branched into two, the amount of light can also be increased in such a way that the number of light sources is increased and the entrance end of the connecting light guide is further branched.

In the second embodiment, the multi-fiber is used for the connecting light guide. Where a number of fibers are used in a bundle, the loss of the amount of light will be caused at the entrance end of the light guide because the core share is not 100%. Hence, for example, when a liquid light guide which is the single fiber, rather than the multi-fiber, is used, further efficiency is achieved.

The diameter of the connecting light guide and the magnification of the connecting optical system are set so that the highest efficiency is attained when the light guide cable has a diameter of 3.5 mm and an NA of 0.66. However, their optimum settings vary with the kind of the light guide cable. The setting of the magnification of the connecting optical system is particularly important, and in order to render the light efficiently incident on the light guide cable, it is desirable to satisfy Conditions (6) and (7).

When the aspherical lenses are used in the connecting optical system, aberration can be suppressed and thus the light can be rendered further efficiently incident on the light guide cable. Also, although the connecting optical system is constructed with lenses in the second embodiment, the conical fiber described in the first embodiment may be used instead of the lenses. In this case, the magnification Mg2 in Condition (7) is replaced by the ratio of an exit diameter h2 to an entrance diameter h1, h2/h1. The conical fiber, like the optical system constructed with lenses, is such that the NA of emergent light increases in rough proportion to the reciprocal of the magnification governed by the ratio of the exit diameter h2 to the entrance diameter h1. For this reason, even when the conical fiber is used, almost the same effect can be secured.

In the second embodiment, reference has been made to the rigid endoscope with the light guide of a branch type by way of example. However, even when a rigid endoscope with a different light guide or a soft endoscope is used, the same effect is brought about. For an endoscope constructed integrally with the light guide, it is only necessary to replace the numerical aperture NA2 in each of Conditions (6) and (7) with the numerical aperture of the light guide on the scope side.

In accordance with the NA of the connecting light guide, the light source optical system is capable of further increasing the amount of light by setting the following condition:

$$0.9 < (NA3/NA1) < 1.1 \quad (19)$$

where NA3 is the numerical aperture of the light source optical system.

Lens data used in the second embodiment are listed below.

(Refer to FIG. 16)

$d_1 = 16.5$, $d_2 = 21$, $d_3 = 5$, $d_4 = 21$, $d_5 = 7.5$
$r_1 = 35.806$, $r_2 = \infty$ (aspherical), $r_3 = \infty$ (aspherical), $r_4 = -32.025$
First lens
$D_1 = 38$, $n_1 = 1.5231$, $v_1 = 58.49$
Second lens
$D_2 = 42$, $n_2 = 1.5231$, $v_2 = 58.49$
Conic constants and aspherical coefficients -continued Second surface $C = 0$, $P = 0$
$B = -3.0397 \times 10^{-2}$, $E = 4.4557 \times 10^{-7}$,
$F = 8.1291 \times 10^{-9}$, $G = 8.1291 \times 10^{-10}$,
$H = -7.086 \times 10^{-17}$, $I = -8.7393 \times 10^{-17}$
Third surface $C = 0$, $P = 0$
$B = 3.6 \times 10^{-2}$, $E = -4.4557 \times 10^{-7}$,
$F = 8.1291 \times 10^{-9}$, $G = -1.1544 \times 10^{-10}$,
$H = 7.086 \times 10^{-17}$, $I = 8.9393 \times 10^{-17}$
(Refer to FIG. 17A)

Outside diameter of parabolic surface $D_M = 25.4$ mm
$d_1 = 21$, $d_2 = 12.9$
$r_1 = \infty$ (aspherical), $r_2 = -32.025$
$f = 21.76$, $D = 42$, $n = 1.5231$, $v = 58.49$
Conic constant and aspherical coefficients $C = 0$, $P = 0$
$B = 3.6 \times 10^{-2}$, $E = -4.4557 \times 10^{-7}$,
$F = 8.1291 \times 10^{-9}$, $G = -1.1544 \times 10^{-10}$,
$H = 7.086 \times 10^{-17}$, $I = 8.9393 \times 10^{-17}$
(Refer to FIG. 17B)

Outside diameter of parabolic surface $D_M = 25.4$ mm
$d_1 = 21$, $d_2 = 13.2$
$r_1 = \infty$ (aspherical), $r_2 = -35.806$
$f = 24.98$, $D = 38$, $n = 1.5231$, $v = 58.49$
Conic constant and aspherical coefficients $C = 0$, $P = 0$
$B = 3.0397 \times 10^{-2}$, $E = -4.4557 \times 10^{-7}$,
$F = -8.1291 \times 10^{-9}$, $G = -8.1291 \times 10^{-10}$,
$H = 7.086 \times 10^{-17}$, $I = 8.7393 \times 10^{-17}$ In the lens data of the above embodiments, $d_1$, $d_2$, ... represent thicknesses of individual lenses or spaces therebetween; $r_1$, $r_2$, ... represent radii of curvature of individual lens surfaces; f represents the focal length of each lens; D, $D_1$, and $D_2$ represent outside diameters of individual lenses; n, $n_1$, $n_2$, ... represent refractive indices of individual lenses; and $v$, $v_1$, $v_2$, ... represent Abbe's numbers of individual lenses.

Also, the configuration of each of the aspherical surfaces in the embodiments is given by $$X = \frac{CY^2}{1 + \sqrt{1 - PC^2 Y^2}} + BY^2 + EY^4 + FY^6 + GY^8 + HY^{10} + IY^{12}$$

where X is the coordinate in the direction of the optical axis, Y is the coordinate in the direction normal to the optical axis, C is the curvature (=1/r) at the vertex of the aspherical surface, P is a conic constant, and B, E, F, G, H, and I are aspherical coefficients.

What is claim is:

1. An illumination system for endoscopes, comprising:
    a light source device having an arc discharge lamp and a light source optical system;
    a light guide cable; and
    a rigid endoscope provided with a light guide on a scope side and an objective optical system, using lenses as a relay optical system,
    said light source optical system projecting a light-emitting section of said arc discharge lamp on an entrance face of said light guide cable at a magnification of approximately 1x, and said light guide cable satisfying the following conditions:

$$0.25 \times Mg1^{1/2} < D_L/D_S < 0.5 \times Mg1^{1/2}$$

$$0.8 < Mg1 \times (D_C/D_L) < 1.2$$

where $D_S$ is an outside diameter of a scope, $D_C$ is a diameter of said light guide cable, $D_L$ is a diameter of said light guide on the scope side, and Mg1 is a projection magnification of an optical element interposed between said light guide cable and said light guide on the scope side.

2. An illumination system for endoscopes, comprising:
- a light source device having an arc discharge lamp and a light source optical system;
- a light guide cable; and
- a rigid endoscope provided with a light guide on a scope side and an objective optical system, using an image fiber as a relay optical system,
- said light source optical system projecting a light-emitting section of said arc discharge lamp on an entrance face of said light guide cable at a magnification of approximately 1×, and said light guide cable satisfying the following conditions:

$$0.4 \times Mg1^{1/2} < D_L/D_S < 0.6 \times Mg1^{1/2}$$

$$0.8 < Mg1 \times (D_C/D_L) < 1.2$$

where $D_S$ is an outside diameter of a scope, $D_C$ is a diameter of said light guide cable, $D_L$ is a diameter of said light guide on the scope side, and Mg1 is a projection magnification of an optical element interposed between said light guide cable and said light guide on the scope side.

3. An illumination system for endoscopes, comprising:
- a light source device having an arc discharge lamp and a light source optical system;
- a light guide cable of a single fiber; and
- a rigid endoscope provided with a light guide on a scope side, including an objective optical system and a relay optical system,
- said light source optical system projecting a light-emitting section of said arc discharge lamp on an entrance face of said light guide cable of the single fiber at a magnification of approximately 1×, and said light guide cable of the single fiber satisfying the following conditions:

$$D_L/D_S < 0.4 \times Mg1$$

$$Mg1 \times D_C < D_L$$

where $D_S$ is an outside diameter of a scope, $D_C$ is a diameter of said light guide cable of the single fiber, $D_L$ is a diameter of said light guide on the scope side, and Mg1 is a projection magnification of an optical element interposed between said light guide cable of the single fiber and said light guide on the scope side.

4. An illumination system for endoscopes, comprising:
- at least one light source device provided with a light source optical system using an arc discharge lamp;
- a connecting light guide whose entrance end is branched in accordance with the number of light source devices; and
- a connecting optical system for rendering light emerging from said connecting light guide incident on an entrance end of a light guide cable,
- said illumination system satisfying the following conditions:

$$NA2 < NA1$$

$$0.8 < (NA2/NA1) \times Mg2 < 1.2$$

where NA1 is a numerical aperture of said connecting light guide, Mg2 is a projection magnification of said connecting optical system, and NA2 is a numerical aperture of said light guide cable.

5. An illumination system for endoscopes according to claim 1, wherein an outside diameter $D_R$ of said relay optical system and the diameter $D_L$ of said light guide on the scope side satisfy the following condition:

$$0.3 \times Mg1^{1/2} < D_L/D_R < 0.7 \times Mg1^{1/2}$$

6. An illumination system for endoscopes according to claim 2, wherein an outside diameter $D_R$ OF said relay optical system and the diameter $D_L$ Of said light guide on the scope side satisfy the following condition:

$$0.5 \times Mg1^{1/2} < D_L/D_R < 0.9 \times Mg1^{1/2}$$

7. An illumination system for endoscopes according to claim 3, wherein an outside diameter $D_R$ of said relay optical system and the diameter $D_L$ of said light guide on the scope side satisfy the following condition:

$$0.1 \times Mg1^{1/2} < D_L/D_R < 0.5 \times Mg1^{1/2}$$

8. An illumination system for endoscopes according to any one of claims 1–3, wherein a pipe of said rigid endoscope in which said objective optical system and said relay optical system are encased has a thickness of at least 0.15 mm.

9. An illumination system for endoscope according to any one of claims 1–3, wherein said light source optical system is placed so that an arc axis of said arc discharge lamp is perpendicular to an optical axis.

10. An illumination system for endoscopes according to claim 9, wherein said light source optical system projects an image of the light-emitting section of said arc discharge lamp on the entrance end face of said light guide cable at a magnification of approximately 1×.

11. An illumination system for endoscopes according to claim 10, wherein said arc discharge lamp is a xenon lamp.

12. An illumination system for endoscopes according to claim 4, further satisfying the following condition:

$$0.9 < (NA3/NA1) < 1.1$$

where NA3 is a numerical aperture of said light source optical system.

* * * * *